United States Patent [19]

Schraml-Marth

[11] Patent Number: 5,565,024
[45] Date of Patent: Oct. 15, 1996

[54] COLOR LUSTER PIGMENTS

[75] Inventor: Matthias Schraml-Marth, Zwingenberg, Germany

[73] Assignee: Merck Patent Gesellschaft Mit Beschrankter Haftung, Darmstadt, Germany

[21] Appl. No.: 426,403

[22] Filed: Apr. 21, 1995

[30] Foreign Application Priority Data

Apr. 22, 1994 [DE] Germany ............ 44 14 114.9

[51] Int. Cl.⁶ ............ C09B 67/22; C08K 3/10; A61K 7/021; D06P 1/44
[52] U.S. Cl. ............ 106/415; 106/417; 106/489; 428/403; 428/404; 428/406
[58] Field of Search ............ 106/415, 417, 106/489; 428/403, 404, 406

[56] References Cited

PUBLICATIONS

Abstract of DE 1,467,468, Derwent Abstract, Jun. 28, 1961.
Abstract of DE 2,009,566, Derwent Abstract, Feb. 28, 1970.
Abstract of DE 4,135,742, Derwent Abstract, May 6, 1993.
Abstract of SU 1699930, Derwent Abstract, Dec. 23, 1991.

*Primary Examiner*—Melissa Bonner
*Attorney, Agent, or Firm*—Millen, White, Zelano & Branigan, P.C.

[57] ABSTRACT

The present invention relates to color luster pigments which, through the incorporation of glass formers, exhibit enhanced luster and also high color strength and transparency.

13 Claims, No Drawings

COLOR LUSTER PIGMENTS

The present invention relates to color luster pigments which, through the incorporation of glass formers, exhibit enhanced luster and also a high color strength and transparency.

BACKGROUND OF THE INVENTION

Pearl luster pigments consist typically of 200 to 1000 nm thick platelet-shaped substrates coated with 50 to 300 nm thick, highly light-refractive metal oxides or metal oxide mixtures in different oxidation states. The optical properties of these pigments are decisively determined by the refractive index of the metal oxide layer. In contradistinction to metal oxide layers produced by chemical vapor deposition (CVD) or physical vapor deposition (PVD), which have high densities and hence refractive indices which are close to the optimum, the deposition of metal oxides onto platelet-shaped substrates is effected by titration of aqueous, usually acidic, metal salt solutions with sodium hydroxide solution in the presence of a substrate, as described for example in DE 14 67 468 and DE 20 09 566.

The character of this aqueous precipitation process does not make it possible to obtain similarly dense layers as in the CVD or PVD processes, and thus the resulting layers exhibit in some instances appreciable porosity. The density and hence the refractive index of such porous metal oxide layers is therefore distinctly below the maximum values which can be achieved. The ability of these pigments to reflect incident light decreases and the color strength and brilliance also decrease. Also, cracks in such metal oxide layers lead to the scattering of light, resulting in reduced transparency.

It is known that boron-containing admixtures activate sintering processes in $Fe_2O_3$ crystals and effect the formation of crack-free polycrystalline $Fe_2O_3$ films.

SU 16 999 930 A1 discloses red pigments of enhanced pearl luster which are based on iron oxide-coated mica platelets aftercoated with $B_2O_3$. The boron-containing iron oxide pigments are calcined at temperatures between 600° and 900° C. in the presence of air to enhance the luster and lightness.

DE 41 35 742 A1 describes $B_2O_3$-doped iron oxide pigments with a particularly smooth surface. The magnetite pigments, produced by the nitrobenzene process, can be converted into red pigments of various tints by subsequent calcination in air.

SUMMARY OF THE INVENTION

It is therefore an object of the present invention to find pigments of enhanced color strength, luster and transparency which are free of the abovementioned disadvantages.

Upon further study of the specification and appended claims, further objects and advantages of this invention will become apparent to those skilled in the art.

It has now been surprisingly found that the incorporation of glass formers into the metal oxide layer of coated substrates leads to a dramatic improvement in the optical properties of the resulting materials. The glass formers activate sintering processes at elevated temperatures, causing the metal oxide layer on the substrate to become densified. Cracks and embedded voids are thus eliminated. As well as the color strength and luster, which correlate directly with the refractive index, the transparency is enhanced by providing this very compact metal oxide layer.

The present invention accordingly provides in one embodiment color luster pigments based on substrates coated with one or more metal oxides or metal oxide mixtures, characterized in that the metal oxide layer contains, e.g. is doped, with borosilicates or is provided with an aftercoating containing borosilicates.

The present invention further provides a process for producing the pigments of the invention, which is characterized in that the substrate suspended in an aqueous solution has added to it in succession or simultaneously one or more metal salt solutions and a boron-oxygen compound in the presence of a water-soluble alkali or alkaline earth metal salt under conditions leading to the deposition of a metal oxide or metal oxide mixture and of a borate on the substrate, an aftercoating is carried out with $SiO_2$, and then the pigment is separated off, washed, dried and calcined at temperatures of about 500° C. or more.

The boron and silicon components form a $B_2O_3/SiO_2$ melt at conventional calcination temperatures. The calcination temperature is dependent upon formation of borosilicate glasses. These fluid phases induce viscous sintering, resulting in densification of the metal oxide layers. Besides color, the elimination of pores in the metal oxide layers enhances the transparency of the pigments.

Suitable base substrates for the coating include opaque and transparent non-platelet-shaped substances. Preferred substrates of this kind are sheet silicates. Also included are, optionally metal oxide-coated, platelet-shaped materials. Particularly suitable are mica, talc, kaolin, bismuth oxychloride, glass, $SiO_2$ or synthetic ceramic flakes, synthetic support free platelets or other comparable materials. It is also possible to use metal platelets, for example aluminum platelets or platelet-shaped metal oxides, for example platelet-shaped iron oxide or mica. The substrates may be optionally coated with colored or colorless metal oxides such as $TiO_2$, $Fe_2O_3$, $SnO_2$, $CR_2O_3$, $ZnO$ and other metal oxides, alone or mixed in a single layer or in successive layers. These pigments, which are known as pearl luster pigments, are known for example from the German Patents and Patent Applications 14 67 468, 19 59 998, 20 09 566, 22 14 545, 22 15 191, 22 44 298, 23 13 331, 25 22 572, 31 37 808, 31 37 809, 31 51 343, 31 51 354, 31 51 355, 32 11 602 and 32 35 017.

The platelet-shaped substrates preferably have a thickness of about 0.1–5 μm, in particular of about 0.2–4.5 μm. The extension in the other two dimensions is usually of about 1–250 μm, in particular, of about 2–200 μm.

The incorporation of the glass formers into or on the metal oxide layer of the substrate can be carried out in several ways.

To produce the pigments of the invention, first an aqueous suspension of the substrate is prepared. To the aqueous suspension of the substrate are added in succession or simultaneously one or more metal salt solutions and a boron-oxygen compound in the presence of a water-soluble alkali or alkaline earth metal salt while the pH of the reaction mixture is maintained by simultaneous addition of an acid or base within a range which causes the metal salt to hydrolyte. This precipitates the metal oxide and a borate onto the substrate surface either in succession or simultaneously. This is followed by the aftercoating with silicon dioxide.

The glass formers, e.g., $B_2O_3$ and $SiO_2$, can also both be homogeneously incorporated into the metal oxide layer by adding the amount of $SiO_2$ required in the form of an aqueous silicon solution to the acid or base solution required for keeping the pH constant.

Also, it is possible first to form the metal oxide layer by precipitation from metal salts and then add the boron-oxygen and SiO$_2$ components together and calcine to form a borosilicate aftercoating.

After the removal, washing and drying of the coated substrates, the pigments are calcined preferably at temperatures of about 500° C. or more, preferably about 800°–850° C., to form borosilicate glass melts which, as a liquid phase, induce sintering processes within the metal oxide layer.

The calcining temperature generally depends on the thickness of the deposited layer. The calcining time can range from a few minutes to several hours, but is preferably between 20 and 120 minutes.

As metal salts from which the hydroxides can be precipitated it is possible to use all water-soluble salts which are hydrolyzable by bases or acids. Suitable metal salts are in particular those of titanium, iron, aluminum, zirconium, chromium, nickel, cobalt and/or tin.

The process of the invention is preferably carried out with the alkaline earth metal and alkali metal salts being the chlorides and nitrates and also other water-soluble compounds.

Suitable boron-oxygen compounds are preferably boric acid salts of polyacids. The alkali metal borates are particularly preferred since these generally still exhibit good solubility in water. The preferred alkali metal borate is disodium tetraborate Na$_2$B$_4$O$_7$×10 H$_2$O (borax).

The silicon dioxide is added to the reaction solution in the form of a water-soluble inorganic silicon compound. Suitable examples are the commercially available aqueous solutions of alkali metal silicates known as "waterglass", for example potassium waterglass and sodium waterglass.

The temperature of the reaction solution is not very critical and customarily is about 20°–80° C., but it is preferred to carry out the precipitation at somewhat higher temperatures, preferably about 40°–90° C., since the solubility of the alkali metal borates increases with the temperature of the solvent. The precipitation is generally carried out at a pH of about 3–12. Owing to the weakly basic character of the borate, the pH of the reaction solution may rise slightly, but adding acids, preferably mineral acids, in particular HCl, it is an easy matter to keep the pH at a constant level.

The glass formers, the borosilicate, can be provided on the substrate not only as an interlayer but also in the form of an aftercoating.

The proportion of glass formers, i.e., borosilicate, based on the total pigment is preferably about 0.05–5 mass percent, particularly preferably about 3 mass percent.

All conceivable B$_2$O$_3$:SiO$_2$ ratios can be used in the doping or coating. However, a positive effect on color strength, luster and transparency can be observed in particular when the mass ratio of boron (III) oxide and silicon dioxide is set in such a way that calcining temperatures of about 500° C. or more lead to flowable melts of boron(III) oxide and silicon dioxide.

Preference is in particular given to mass ratios as encountered in commercially available borosilicate glasses, for example Pyrex glass. The mass ratios of SiO$_2$/B$_2$O$_3$ therein are 10:1–0.1:1, preferably 4:1–0.4:1.

The color luster pigments produced by the process of the invention are notable for elevated values for color strength and luster and also for their high transparency. They are compatible with a multiplicity of color systems, preferably from the sector of coatings, paints and printing inks.

Plastics and plastics systems pigmented with the pigments of the invention remain substantially free of any yellowing even over prolonged periods, in contradistinction to other stabilizing methods.

The present invention thus also provides for the use of the pigments of the invention in formulations such as paints, coatings, printing inks, plastics and cosmetics.

The present invention thus further provides formulations comprising the pigments of the invention.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. P 44 14 114.9, filed Apr. 22, 1994, are hereby incorporated by reference.

EXAMPLES

Example 1

100 g of mica of the particle size 10–60 μm are suspended in 2 l of water and heated to 75° C. 5% HCl is used to set a pH of 4 and then 2 l of an aqueous FeCl$_3$ solution (Fe content: 2.1 mass percent) are metered in over 500 minutes. During the addition of the FeCl$_3$ solution the pH of the suspension is held at pH 4 by addition of 30% NaOH. This is followed by stirring for 15 minutes and then the pH is adjusted to 6.7 with 5% NaOH. This is followed by the simultaneous but separate metered addition of a solution of 2.5 g of CaCl$_2$×H$_2$O in 200 ml of water over 60 minutes. The batch is subsequently stirred for 15 minutes and adjusted to pH 9 with 5% NaOH. A solution of 5.4 ml of sodium waterglass (185 g/l) in 75 ml of water is metered in over 30 minutes while the pH is maintained at 9 with 5% HCl. After the addition the batch is stirred for 15 minutes and adjusted to pH 6.5 with 5% HCl. The reaction product is filtered off, dried and calcined at 850° C.

Example 2

100 g of mica of the particle size 10–60 μm are suspended in 2 l of water and heated to 75° C. 5% HCl is used to set a pH of 4 and then 1.6 liters of an aqueous FeCl$_3$ solution (Fe content: 2.1 mass percent) are metered in over 400 minutes. During the addition of the FeCl$_3$ solution the pH of the suspension is held at pH 4 by addition of 30% NaOH. This is followed by stirring for 15 minutes and then the pH is adjusted to 6.7 with 5% NaOH. This is followed by the simultaneous metered addition of a solution of 6.6 g of Na$_2$B$_4$O$_7$×10 H$_2$O in 200 ml of water and a solution of 2.5 g of CaCl$_2$×2 H$_2$O in 200 ml of water over 60 minutes. The batch is subsequently stirred for 15 minutes and again set to pH 4 with 5% HCl. The remaining 400 ml of the FeCl$_3$ solution are metered in over 100 minutes. Stirring is continued for 15 minutes, and the pH is adjusted to 9 with 5% NaOH. A solution of 5.4 ml of sodium waterglass (185 g/l) in 75 ml of water is metered in over 30 minutes while the pH is maintained at 9 with 5% HCl. After the addition the batch is stirred for 15 minutes and adjusted to pH 6.5 with 5% HCl. The reaction product is filtered off, dried and calcined at 850° C.

Example 3

100 g of mica of the particle size 10–60 μm are suspended in 2 l of water and heated to 75° C. 5% HCl is used to set a pH of 4 and then 2 l of an aqueous FeCl$_3$ solution (Fe content: 2.1 mass percent) are metered in over 500 minutes. During the addition of the $FeCl_3$ solution the pH of the suspension is held at pH 4 by addition of 30% NaOH. This is followed by stirring for 15 minutes and then the pH is adjusted to 6.7 with 5% NaOH. This is followed by the simultaneous metered addition of a solution of 8.2 g of $Na_2B_4O_7 \times 10\ H_2O$ in 200 ml of water over 60 minutes. The batch is subsequently stirred for 15 minutes and adjusted to pH 9 with 5% NaOH. A solution of 16.2 ml of sodium waterglass (185 g/l) in 100 ml of water is metered in over 30 minutes while the pH is maintained at 9 with 5% HCl. After the addition the batch is stirred for 15 minutes and adjusted to pH 6.5 with 5% HCl. The reaction product is filtered off, dried and calcined at 850° C.

Example 4

100 g of mica of the particle size 10–60 μm are suspended in 2 l of water and heated to 75° C. 5% HCl is used to set a pH of 4 and then 2.5 l of an aqueous $FeCl_3$ solution (Fe content: 2.1 mass percent) in which, prior to the coating, 1.0 g of orthoboric acid was dissolved are metered in over 625 minutes. During the metered addition of the FeCl solution of the pH of the suspension is kept at pH 4 by addition of 30% NaOH. The batch is subsequently stirred for 15 minutes and then adjusted to pH 9 with 5% NaOH. A solution of 5.4 ml of sodium waterglass (185 g/l) in 75 ml of water is metered in over 30 minutes while the pH is maintained at 9 with 5% HCl. After the addition the batch is stirred for 15 minutes and adjusted to pH 6.5 with 5% HCl. The reaction product is filtered off, dried and calcined at 850° C.

Example 5

100 g of mica of the particle size 10–60 μm are suspended in 2 l of water and heated to 75° C. 5% HCl is used to set a pH of 4 and then 2.3 l of an aqueous $FeCl_3$ solution (Fe content: 2.1 mass percent) in which, prior to the coating, 5.0 g of orthoboric acid were dissolved are metered in over 570 minutes. During the metered addition of the $FeCl_3$ solution the pH of the suspension is kept at pH 4 by addition of 30% NaOH. The batch is subsequently stirred for 15 minutes and then adjusted to pH 9 with 5% NaOH. A solution of 5.4 ml of sodium waterglass (185 g/l) in 75 ml of water is metered in over 30 minutes while the pH is maintained at 9 with 5% HCl. After the addition the batch is stirred for 15 minutes and adjusted to pH 6.5 with 5% HCl. The reaction product is filtered off, dried and calcined at 850° C.

Example 6

100 g of mica of the particle size 10–60 μm are suspended in 2 l of water and heated to 75° C. 5% HCl is used to set a pH of 4 and then 2.5 l of an aqueous $FeCl_3$ solution (Fe content: 2.1 mass percent) in which, prior to the coating, 1.6 g of $Na_2B_4O_7 \times 10\ H_2O$ were dissolved are metered in over 625 minutes. During the metered addition of the $FeCl_3$ solution the pH of the suspension is kept at pH 4 by addition of 30% NaOH. The batch is subsequently stirred for 15 minutes and then adjusted to pH 9 with 5% NaOH. A solution of 16.2 ml of sodium waterglass (185 g/l) in 75 ml of water is metered in over 30 minutes while the pH is maintained at 9 with 5% HCl. After the addition the batch is stirred for 15 minutes and adjusted to pH 6.5 with 5% HCl. The reaction product is filtered off, dried and calcined at 850° C.

Example 7

100 g of mica of the particle size 10–60 μm are suspended in 2 l of water and heated to 75° C. 5% HCl is used to set a pH of 4 and then 2.5 l of an aqueous $FeCl_3$ solution (Fe content: 2.1 mass percent) in which, prior to the coating, 1.6 g of $Na_2B_4O_7 \times 10\ H_2O$ were dissolved are metered in over 625 minutes. During the metered addition of the $FeCl_3$ solution the pH of the suspension is kept at pH 4 by addition of 30% NaOH. The batch is subsequently stirred for 15 minutes and then adjusted to pH 9 with 5% NaOH. A solution of 27.0 ml of sodium waterglass (185 g/l) in 75 ml of water is metered in over 30 minutes while the pH is maintained at 9 with 5% HCl. After the addition the batch is stirred for 15 minutes and adjusted to pH 6.5 HCl. The reaction product is filtered off, dried and calcined at 850° C.

Example 8

100 g of mica of the particle size 10–60 μm are suspended in 2 l of water and heated to 75° C. 5% HCl is used to set a pH of 4 and then 2.5 l of the aqueous $FeCl_3$ solution (Fe content: 2.1 mass percent) in which, prior to the coating, 1.6 g of $Na_2B_4O_7 \times 10\ H_2O$ were dissolved are metered in over 625 minutes. During the metered addition of the $FeCl_3$ solution the pH of the suspension is kept to pH 4 by addition of 30% NaOH. The NaOH used was admixed with 6.2 ml of sodium waterglass (185 g/l) prior to the coating. After the addition, the batch is stirred for 15 minutes and adjusted to pH 6.5 with 5% HCl. The reaction product is filtered off, dried and calcined at 850° C.

Example 9

100 g of mica of the particle size 10–60 μm are suspended in 2 l of water and heated to 75° C. 5% HCl is used to set a pH of 2.2 and then 800 ml of an aqueous $TiCl_4$ solution ($TiCl_4$ content: 350 g/l) in which, prior to the coating, 1.4 g of $Na_2B_4O_7 \times 10\ H_2O$ were dissolved are metered in over 410 minutes. During the metered addition of the $TiCl_4$ solution the pH of the suspension is kept at pH 2.2 by addition of 30% NaOH. This is followed by 15 minutes of stirring and then the pH is adjusted to 9 with 5% NaOH. A solution of 5.4 ml of sodium waterglass (373 g of $SiO_2$/l) in 120 ml of water is metered in over 30 minutes while the pH is kept at pH 9 with 5% HCl. After the addition the batch is stirred for 15 minutes and adjusted to pH 6.5 with 5% HCl. The reaction product is filtered off, dried and calcined at 800° C.

Example 10

100 g of mica of the particle size 10–60 μm are suspended in 2 l of water and heated to 75° C. 5% HCl is used to set a pH of 2.2 and then 800 ml of an aqueous $TiCl_4$ solution ($TiCl_4$ content: 350 g/l) in which, prior to the coating, 1.4 g of $Na_2B_4O \times 10\ H_2O$ were dissolved are metered in over 410 minutes. During the metered addition of the $TiCl_4$ solution the pH of the suspension is kept at pH 2.2 by addition of 30% NaOH. This is followed by 15 minutes of stirring and then the pH is adjusted to 9 with 5% NaOH. A solution of 8 ml of sodium waterglass (373 g of $SiO_2$/l) in 120 ml of water is metered in over 30 minutes while the pH is kept at pH 9 with 5% HCl. After the addition the batch is stirred for 15 minutes and adjusted to pH 6.5 with 5% HCl. The reaction product is filtered off, dried and calcined at 800° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A color luster pigment comprising a substrate coated with one or more layers of one or more metal oxides or metal oxide mixtures, wherein a metal oxide layer contains a borosilicate, or is aftercoated to provide layers containing a borosilicate.

2. The color luster pigment according to claim 1, wherein the proportion of borosilicate based on the total pigment is 0.05–5 mass percent.

3. The color luster pigment according to claim 1, wherein the substrate is platelet-shaped.

4. The color luster pigment according to claim 3, wherein the platelet-shaped substrate is mica or $SiO_2$ flakes.

5. The pigment of claim 1, wherein the metal oxide or metal oxide mixture coating comprises an oxide of titanium, iron, aluminum, zirconium, chromium, nickel cobalt or tin.

6. A process for producing a color pigment according to claim 1, comprising adding to an aqueous suspension of the substrate, a) in succession or simultaneously, one or more metal salt solutions and a boron-oxygen compound in the presence of water-soluble alkali or alkaline earth metal salt such that a metal oxide or metal oxide mixture and a borate are deposited on the substrate, an aftercoating of $SiO_2$ is applied, or b) a solution consisting of one or more metal salts and a water-soluble boron-oxygen compound and simultaneously but separately a water-soluble silicon compound such that a metal oxide or metal oxide mixture, $B_2O_3$ and $SiO_2$ are deposited on the substrate, and then the pigment is separated off, washed, dried and calcined at temperatures of about 500° C. or more.

7. The process of claim 6, wherein the ratio of $SiO_2$ to $B_2O_3$ in the metal oxide layer is from 0.1:1 to 10:1.

8. A process for producing a pigment of claim 1, comprising calcining a substrate having deposited thereon a metal oxide or metal oxide mixture, a borate or $B_2O_3$ and $SiO_2$.

9. The process of claim 6, according to part a), wherein the alkali or alkaline earth metal salt is a chloride or nitrate.

10. The process of claim 6, wherein the boron-oxygen compound is an alkali metal borate or boric acid salt of a polyacid.

11. The process of claim 6, according to part b), wherein the water-soluble silicon compound is an alkali metal silicate.

12. A method for inhibiting yellowing in plastics and plastics systems comprising incorporating therein a pigment according to claim 1.

13. A coating, coloring, plastic or cosmetic formulation comprising a pigment according to claim 1.

* * * * *